United States Patent
Akabane

(10) Patent No.: US 10,047,184 B2
(45) Date of Patent: Aug. 14, 2018

(54) FILM-FORMING COMPOSITION AND COSMETIC

(71) Applicant: SHIN-ETSU CHEMICAL CO., LTD., Tokyo (JP)

(72) Inventor: Emi Akabane, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 38 days.

(21) Appl. No.: 15/503,883

(22) PCT Filed: Jun. 29, 2015

(86) PCT No.: PCT/JP2015/003243
§ 371 (c)(1),
(2) Date: Feb. 14, 2017

(87) PCT Pub. No.: WO2016/035232
PCT Pub. Date: Mar. 10, 2016

(65) Prior Publication Data
US 2017/0240677 A1 Aug. 24, 2017

(30) Foreign Application Priority Data
Sep. 4, 2014 (JP) ................... 2014-179840

(51) Int. Cl.
C08F 283/12 (2006.01)
A61K 8/899 (2006.01)
A61Q 19/00 (2006.01)
C08G 77/28 (2006.01)

(52) U.S. Cl.
CPC ............ *C08F 283/12* (2013.01); *A61K 8/899* (2013.01); *A61Q 19/00* (2013.01); *C08G 77/28* (2013.01)

(58) Field of Classification Search
CPC ..................................................... C08G 77/28
See application file for complete search history.

(56) References Cited

U.S. PATENT DOCUMENTS

| 5,362,485 | A | 11/1994 | Hayama et al. |
| 6,147,142 | A | 11/2000 | Geck et al. |
| 2003/0139481 | A1 | 7/2003 | Osawa |
| 2009/0036615 | A1 | 2/2009 | Miyadai et al. |
| 2009/0196911 | A1 | 8/2009 | Loubert et al. |
| 2010/0130693 | A1* | 5/2010 | Yamada ............... A61K 8/064 525/326.5 |
| 2010/0284957 | A1 | 11/2010 | Yamada et al. |
| 2015/0133594 | A1 | 5/2015 | Ihara et al. |

FOREIGN PATENT DOCUMENTS

| EP | 2028245 A2 | 2/2009 |
| JP | S63-313713 A | 12/1988 |
| JP | S64-43342 A | 2/1989 |
| JP | H03-126735 A | 5/1991 |
| JP | H04-45155 A | 2/1992 |
| JP | H06-92825 A | 4/1994 |
| JP | H07-268044 A | 10/1995 |
| JP | 2636948 B2 | 8/1997 |
| JP | 2767633 B2 | 6/1998 |
| JP | H11-508641 A | 7/1999 |
| JP | 2976146 B2 | 11/1999 |
| JP | 2001-151830 A | 6/2001 |
| JP | 3218872 B2 | 10/2001 |
| JP | 2003-212998 A | 7/2003 |
| JP | 2008-274116 A | 11/2008 |
| JP | 2009-046662 A | 3/2009 |
| JP | 2009-132850 A | 6/2009 |
| JP | 2009-540052 A | 11/2009 |
| JP | 4666660 B2 | 4/2011 |
| JP | 2012-072081 A | 4/2012 |
| JP | 2013-245279 A | 12/2013 |
| WO | 2008/134428 A1 | 11/2008 |
| WO | 2009/086260 A2 | 7/2009 |

OTHER PUBLICATIONS

Mar. 7, 2017 International Preliminary Report on Patentability issued in International Patent Application No. PCT/JP2015/003243.
Sep. 29, 2015 International Search Report issued in International Patent Application No. PCT/JP2015/003243.
Mar. 19, 2018 Extended European Search Report issued in European Patent Application No. 15837437.1.
Database WPI, Week 199213, Thomson Scientific, London, GB, AN 1992-101593, XP002778732, 1992.

* cited by examiner

*Primary Examiner* — Kuo Liang Peng
(74) *Attorney, Agent, or Firm* — Oliff PLC

(57) ABSTRACT

A film-forming composition containing a polymer obtained by polymerizing (A) 5 to 80 mass % of a silicone resin having an $R_3SiO_{1/2}$ unit, an $R_2R'SiO_{1/2}$ unit, and an $SiO_2$ unit, where R may be the same or different and represents a monovalent hydrocarbon group having 1 to 6 carbon atoms, and R' represents a —$C_3H_6SH$ group, wherein a total amount of the $R_3SiO_{1/2}$ unit, $R_2R'SiO_{1/2}$ unit, and $SiO_2$ unit is 80 mol % or more with respect to all structural units, and a mole ratio expressed by (sum of $R_3SiO_{1/2}$ unit and $R_2R'SiO_{1/2}$ unit)/($SiO_2$ unit) ranges from 0.5 to 1.5 and (B) 20 to 95 mass % of one or more radically polymerizable compounds, wherein component (B) includes (B-1) one or more radically polymerizable monomers having no SiO unit in a structure thereof. This composition is capable of forming a transparent film that is excellent in adhesiveness without exhibiting stickiness and secondary adhesion.

20 Claims, No Drawings

FILM-FORMING COMPOSITION AND COSMETIC

TECHNICAL FIELD

The present invention relates to a film-forming composition and a cosmetic, and more particularly to a film-forming composition that imparts a surface protecting effect useful in fields such as cosmetics and medicine.

BACKGROUND ART

An organic silicone resin has been conventionally used as a coating agent for giving water repellency to skin or hair to protect their surfaces. Examples of the organic silicone resin include a resin (hereinafter, referred to as a silicone resin) composed of M unit expressed by general formula $R^X_3SiO_{1/2}$ (where $R^X$ represents a hydrogen atom or an organic group), Q unit expressed by $SiO_2$, D unit expressed by $R^X_2SiO$, and T unit expressed by $R^XSiO_{3/2}$; and a resin (hereinafter, referred to as a silicone-modified acrylic polymer) mainly composed of a copolymer of a silicone macromonomer having a (meth)acrylic group with other polymerizable monomer.

A cosmetic containing the organic silicone resin with the silicone resin structure is characterized by inhibiting secondary adhesion and giving water repellency. However, the silicone resin is a rigid resin having low flexibility and is difficult to form a transparent and flexible film. Thus, this resin has difficulties in feeling of use as well as adhesiveness to the skin or hair in that the cosmetic containing this resin gives tension feeling and easily causes cracks and separation of the film formed by the cosmetic. To remedy the difficulties, compositions containing a highly polymerized polysiloxane in addition to the silicone resin have been proposed (Patent Documents 1 to 3, for example). These compositions can significantly improve adhesiveness of the resulting film, but still have problems of stickiness and secondary adhesion due to the highly polymerized polysiloxane.

In addition, a composition containing a specific silicone resin and a specific polysiloxane and oil material with a specific ratio has been proposed (Patent Document 4, for example). This composition can form a film having significantly improved adhesiveness and stickiness, but is inadequate to meet recent requirements of users.

On the other hand, the silicone-modified acrylic polymer enables formation of a film having water repellency, flexibility, and high adhesiveness and makes a cosmetic containing this polymer smooth and glossy. In particular, the silicone-modified acrylic polymer has been developed to have miscibility with various oil materials (Patent Documents 5 to 8). However, a film formed by such a silicone-modified acrylic polymer has low strength and easily causes cosmetic deterioration. Thus, this polymer is still inadequate to meet the recent requirements of users.

To make the best use of the silicone resin and the silicone-modified acrylic polymer, a mixture thereof is proposed as a film-forming agent to form a film having non-stickiness, adhesiveness, and excellent abrasion resistance. However, since the silicone resin is not miscible with the silicone-modified acrylic polymer, this mixture is inadequate to form a transparent film.

CITATION LIST

Patent Literature

Patent Document 1: Japanese Unexamined Patent publication (Kokai) No. S63-313713
Patent Document 2: Japanese Unexamined Patent publication (Kokai) No. S64-43342
Patent Document 3: Japanese Unexamined Patent publication (Kokai) No. H04-45155
Patent Document 4: Japanese Patent No. 4666660
Patent Document 5: Japanese Unexamined Patent publication (Kokai) No. 2009-46662
Patent Document 6: Japanese Unexamined Patent publication (Kokai) No. 2012-72081
Patent Document 7: Japanese Patent No. 2767633
Patent Document 8: Japanese Patent No. 2976146

SUMMARY OF INVENTION

Technical Problem

The present invention was accomplished in view of the above-described problems. It is an object of the present invention to provide a film-forming composition capable of forming a transparent film that is excellent in adhesiveness to the skin, hair, or the like and does not exhibit stickiness and secondary adhesion.

Solution to Problem

To solve the foregoing problems, the present invention provides a film-forming composition comprising a polymer obtained by polymerizing:
(A) 5 to 80 mass % of a silicone resin having an $R_3SiO_{1/2}$ unit, an $R_2R'SiO_{1/2}$ unit, and an $SiO_2$ unit, where R may be the same or different and represents a monovalent hydrocarbon group having 1 to 6 carbon atoms, and R' represents a $-C_3H_6SH$ group, in which a total amount of the $R_3SiO_{1/2}$ unit, the $R_2R'SiO_{1/2}$ unit, and the $SiO_2$ unit is 80 mol % or more with respect to all structural units, and a mole ratio expressed by (sum of $R_3SiO_{1/2}$ unit and $R_2R'SiO_{1/2}$ unit)/ ($SiO_2$ unit) ranges from 0.5 to 1.5; and
(B) 20 to 95 mass % of one or more radically polymerizable compounds, wherein
the component (B) includes (B-1) one or more radically polymerizable monomers having no SiO unit in a structure thereof.

Use of this film-forming composition enables formation of a transparent film that is excellent in adhesiveness to the skin, hair, or the like and does not exhibit stickiness and secondary adhesion.

The component (B-1) preferably includes methyl (meth) acrylate.

Such component (B-1) can be suitably used as a structural component of the film-forming composition of the present invention.

The component (B) preferably further includes (B-2) a silicone macromonomer having a radically polymerizable group.

When the component (B) includes (B-2) a silicone macromonomer having a radically polymerizable group, the film-forming composition is especially excellent in abrasion resistance.

The component (B-2) is preferably a silicone macromonomer shown by the following formula (1),

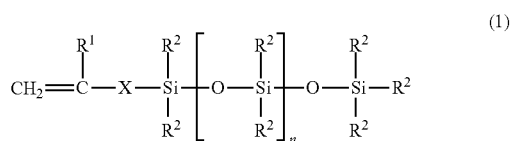

wherein X represents a divalent aromatic group having 6 to 12 carbon atoms or —COOR$^3$— where R$^3$ represents an aliphatic group bonded to Si; R$^1$ represents a hydrogen atom or a methyl group; R$^2$ may be the same or different and represents a fluorine-substituted or unsubstituted alkyl group having 1 to 30 carbon atoms or an aryl group; and "n" represents an integer of 1 to 300.

Such component (B-2) improves reactivity of the polymerization reaction for producing the film-forming composition and allows the composition to have better smoothness and miscibility between the polymer and an oil material. Moreover, a film formed from the composition has little stickiness and high adhesiveness to the skin, hair, or the like.

The film-forming composition may further comprise (C) an oil material. The amount of the component (C) is preferably 1 to 98 mass % with respect to the whole film-forming composition.

Even when (C) an oil material is contained, the film-forming composition of the present invention has little stickiness and excellent water repellency and usability.

The component (C) is preferably silicone oil, light liquid isoparaffin, or both of the silicone oil and the light liquid isoparaffin.

Such component (C) is especially miscible with the polymer of the component (A) and the component (B) and thus favorably used.

Furthermore, the present invention provides a cosmetic comprising the above film-forming composition.

The cosmetic containing the above film-forming composition can form a highly transparent film that is excellent in adhesiveness to the skin, hair, or the like and does not exhibit stickiness and secondary adhesion.

Advantageous Effects of Invention

As mentioned above, the film-forming composition of the present invention is capable of forming a transparent film that is excellent in adhesiveness to the skin, hair, or the like and does not exhibit stickiness and secondary adhesion. Moreover, the film-forming composition of the present invention enables formation of a flexible film without tension feeling on application to the skin, hair, etc. Therefore, the film-forming composition of the present invention is useful to impart water repellency and the surface protecting effect to the skin, hair, or the like in the fields of cosmetic and medicine.

DESCRIPTION OF EMBODIMENTS

As mentioned above, it is desired to develop the film-forming composition capable of forming a transparent film that is excellent in adhesiveness to the skin, hair, or the like and does not exhibit stickiness and secondary adhesion.

The present inventor repeatedly and keenly conducted studies to achieve the above object and consequently found that a film-forming composition containing a polymer obtained by polymerizing (A) a silicone resin and (B) one or more radically polymerizable compounds, which are described below, with a predetermined ratio is capable of forming a transparent film that is excellent in adhesiveness to the skin, hair, or the like and does not exhibit stickiness and secondary adhesion, thereby bringing the present invention to completion.

That is, the present invention is a film-forming composition comprising a polymer obtained by polymerizing:
(A) 5 to 80 mass % of a silicone resin having an R$_3$SiO$_{1/2}$ unit, an R$_2$R'SiO$_{1/2}$ unit, and an SiO$_2$ unit, where R may be the same or different and represents a monovalent hydrocarbon group having 1 to 6 carbon atoms, and R' represents a —C$_3$H$_6$SH group, in which a total amount of the R$_3$SiO$_{1/2}$ unit, the R$_2$R'SiO$_{1/2}$ unit, and the SiO$_2$ unit is 80 mol % or more with respect to all structural units, and a mole ratio expressed by (sum of R$_3$SiO$_{1/2}$ unit and R$_2$R'SiO$_{1/2}$ unit)/(SiO$_2$ unit) ranges from 0.5 to 1.5; and
(B) 20 to 95 mass % of one or more radically polymerizable compounds, wherein
the component (B) includes (B-1) one or more radically polymerizable monomers having no SiO unit in a structure thereof.

Hereinafter, the present invention will be described in detail, but the present invention is not limited thereto.

<Film-Forming Composition>

[(A) Silicone Resin]

The component (A) of the film-forming composition of the present invention has an R$_3$SiO$_{1/2}$ unit, an R$_2$R'SiO$_{1/2}$ unit, and an SiO$_2$ unit, where R may be the same or different and represents a monovalent hydrocarbon group having 1 to 6 carbon atoms, and R' represents a —C$_3$H$_6$SH group. The total amount of the R$_3$SiO$_{1/2}$ unit, the R$_2$R'SiO$_{1/2}$ unit, and the SiO$_2$ unit is 80 mol % or more with respect to all structural units, and the mole ratio expressed by (the sum of R$_3$SiO$_{1/2}$ unit and R$_2$R'SiO$_{1/2}$ unit)/(SiO$_2$ unit) ranges from 0.5 to 1.5.

When the total amount of the three units is less than 80 mol %, the component (A) has low oil-solubility and thus makes it difficult to form a transparent film from the inventive film-forming composition that contains an oil material. Therefore, the total amount of the three units should be 80 mol % or more, preferably 90 mol % or more.

The component (A) may or may not contain an R$_2$SiO unit and/or an RSiO$_{3/2}$ unit.

In the R$_3$SiO$_{1/2}$, R$_2$R' SiO$_{1/2}$, R$_2$SiO, and RSiO$_{3/2}$ units, R represents a monovalent hydrocarbon group having 1 to 6 carbon atoms. Examples thereof include alkyl groups such as methyl, ethyl, propyl, butyl, pentyl, and hexyl; and a phenyl group. A plurality of R in the component (A) may be the same or different from one another. Preferably, 80 mol % or more of all R are methyl groups.

The mole ratio expressed by (the sum of R$_3$SiO$_{1/2}$ unit and R$_2$R'SiO$_{1/2}$ unit)/(SiO$_2$ unit) ranges from 0.5 to 1.5. When the mole ratio is less than 0.5, the component (A) has low oil-solubility and makes it difficult to form an excellent film as mentioned above. When the mole ratio is more than 1.5, the resulting film can have stickiness. Therefore, the mole ratio should range from 0.5 to 1.5, preferably 0.7 to 1.2.

The mole ratio expressed by (R$_2$R'SiO$_{1/2}$ unit)/(R$_3$SiO$_{1/2}$ unit) is preferably, but not particularly limited to, from 0.001 to 0.5, more preferably 0.005 to 0.2, much more preferably 0.01 to 0.1. The component (A) reacts with the component (B) by using SH groups contained in the R$_2$R'SiO$_{1/2}$ unit as reactive groups. Since the SH groups also serve as chain transfer groups, the molecular weight of the film-forming composition and the hardness of its film can be adjusted by the content of the R$_2$R'SiO$_{1/2}$ unit. When the mole ratio expressed by (R$_2$R'SiO$_{1/2}$ unit)/(R$_3$SiO$_{1/2}$ unit) is 0.001 or more, the film-forming composition can form a film with sufficient hardness. When this mole ratio is 0.5 or less, sufficient film-forming property can be obtained.

The component (A) can be readily obtained by hydrolysis condensate of corresponding and known silanes as described in Japanese Patent No. 3218872, although the synthesis method is not limited thereto.

The proportion of the component (A) of the film-forming composition of the present invention is 5 to 80 mass %, preferably 7 to 70 mass %, more preferably 20 to 60 mass %, with respect to the total amount of the component (A) and the component (B). When the proportion of the component (A) is less than 5 mass %, the film has inadequate hardness and is sticky. In addition, the film can have inadequate water repellency due to reduction in water resistance. When the proportion exceeds 80 mass %, a flexible film cannot be easily obtained.

[(B) Radically Polymerizable Compound]

The component (B) of the film-forming composition of the present invention is one or more radically polymerizable compounds that include (B-1) one or more radically polymerizable monomers having no SiO unit in a structure thereof.

(B-1) Radically Polymerizable Monomer Having No SiO Unit in Structure

The radically polymerizable monomer having no SiO unit preferably includes methyl (meth)acrylate. The monomer may include methyl (meth)acrylate alone, or more preferably further includes another radically polymerizable monomer, still more preferably two or more radically polymerizable monomers. When two or more radically polymerizable monomers are included in addition to methyl (meth)acrylate, the proportion of the methyl (meth)acrylate is preferably 30 to 95 mass %, more preferably 40 to 90 mass %, still more preferably 50 to 70 mass %, with respect to the whole component (B-1).

Examples of the radically polymerizable monomer other than methyl (meth)acrylate include (meth)acrylic acid, 2-hydroxyethyl (meth)acrylate, hydroxypropyl (meth)acrylate; (meth)acrylates of alcohols having a linear, branched, or alicyclic hydrocarbon group such as ethyl (meth)acrylate, n-propyl (meth)acrylate, isopropyl (meth)acrylate, n-butyl (meth)acrylate, isobutyl (meth)acrylate, t-butyl (meth)acrylate, 2-ethylhexyl (meth)acrylate, n-hexyl (meth)acrylate, n-octyl (meth)acrylate, cyclohexyl (meth)acrylate, decyl (meth)acrylate, undecyl (meth)acrylate, lauryl (meth)acrylate, tridecyl (meth)acrylate, myristyl (meth)acrylate, pentadecyl (meth)acrylate, palmityl (meth)acrylate, heptadecyl (meth)acrylate, stearyl (meth)acrylate, isostearyl (meth)acrylate, oleyl (meth)acrylate, and behenyl (meth)acrylate; acrylonitrile, vinyl acetate, styrene, vinyl pyrrolidone; acrylamide, diacetone acrylamide, N,N-dimethyl acrylamide, N-t-butyl acrylamide, N-octyl acrylamide, N-t-octyl acrylamide; (meth)acrylates such as tetrahydrofurfuryl (meth)acrylate, isobornyl (meth)acrylate, and glycidyl (meth)acrylate; alkoxyalkyl (meth)acrylates such as ethoxyethyl (meth)acrylate and methoxyethyl (meth)acrylate; monoesters of polyalkyleneglycol and (meth)acrylic acid such as polyethyleneglycol mono(meth)acrylate and polypropylene glycol mono(meth)acrylate; and glyceryl (meth)acrylate.

Other examples of the radically polymerizable monomer other than methyl (meth)acrylate include mono-functional ethylenically unsaturated monomers such as anionic unsaturated monomers, cationic unsaturated monomers, and amphoteric unsaturated monomers, and poly-functional ethylenically unsaturated monomers.

The anionic unsaturated monomer may be exemplified by carboxyl-group-containing unsaturated monomers, sulfonic acid-group-containing monomers, and phosphoric acid-group-containing unsaturated monomers. More specifically, examples of the carboxyl-group-containing unsaturated monomer include unsaturated monocarboxylic acids such as crotonic acid; unsaturated dicarboxylic acids such as itaconic acid, maleic acid, fumaric acid, maleic anhydride, and citraconic acid; monoalkyl esters of unsaturated dicarboxylic acids such as monoalkyl maleate, monoalkyl fumarate, and monoalkyl itaconate; 2-methacryloyloxyethyl succinic acid, 2-(meth)acryloyloxyethyl phthalic acid, β-carboxyethyl acrylate, acryloyloxyethyl succinate, 2-propenoic acid, 3-(2-carboxyethoxy)-3-oxypropyl ester, 2-(meth)acryloyloxyethyl tetrahydrophthalic acid, and 2-(meth)acryloyloxyethyl hexahydrophthalic acid. Examples of the sulfonic acid-group-containing monomer include alkene sulfonic acids such as vinyl sulfonic acid and (meth)allyl sulfonic acid, aromatic vinyl-group-containing sulfonic acid such as α-methylstyrene sulfonic acid, sulfonic acid-group-containing (meth)acrylate monomers, and sulfonic acid-group-containing (meth)acrylamide monomers such as 2-(meth)acrylamide-2-methylpropane sulfonic acid. Examples of the phosphoric acid-group-containing unsaturated monomers include monoesters of methacryloyloxyalkyl phosphoric acids such as (meth)acryloyloxyethyl phosphate.

The cationic unsaturated monomer may be exemplified by primary, secondary, or tertiary amino group-containing unsaturated monomers. Illustrative examples thereof include (meth)allylamine, aminoethyl (meth)acrylate, alkylaminoalkyl (meth)acrylates such as t-butylaminoethyl methacrylate and methylaminoethyl (meth)acrylate, dialkylaminoalkyl (meth)acrylates such as dimethylaminoethyl (meth)acrylate and diethylaminoethyl (meth)acrylate, dialkylaminoalkyl (meth)acryl amides such as dimethylaminoethyl (meth)acrylamide and diethylaminoethyl (meth)acrylamide, amino-group-containing aromatic vinyl monomers such as N,N-dimethylaminostyrene.

Examples of the amphoteric unsaturated monomer include amine derivatives of (meth)acrylates such as dimethylaminoethyl (meth)acrylate, dimethylaminopropyl (meth)acrylate, and diethylaminoethyl (meth)acrylate, (meth)acryl amide derivatives such as dimethylaminoethyl (meth)acrylamide and dimethylaminopropyl (meth)acrylamide, aminomethylpropanol salt of monochloroacetic acid, triethanolamine salt of monochloroacetic acid, monomers modified with halogenated fatty acid salt such as potassium monochloroacetate and sodium monobromopropionate, and monomers modified with lactones such as propiolactone or sultones such as propanesultone.

Examples of the poly-functional ethylenically unsaturated monomer include 1,4-butanediol di(meth)acrylate, 1,6-hexanediol di(meth)acrylate, ethylene glycol di(meth)acrylate, polyethylene glycol (repeating number=2 to 50) di(meth)acrylate, propylene glycol di(meth)acrylate, polypropylene glycol (repeating number=2 to 50) di(meth)acrylate, butylene glycol di(meth)acrylate, dipentyl glycol di(meth)acrylate, neopentyl glycol di(meth)acrylate, trimethylolpropane di(meth)acrylate, methylene bisacrylamide, bisphenol F ethylene oxide (repeating number=2 to 50) modified di(meth)acrylate, bisphenol F propylene oxide (repeating number=2 to 50) modified di(meth)acrylate, bisphenol A ethylene oxide (repeating number=2 to 50) modified di(meth)acrylate, bisphenol A propylene oxide (repeating number=2 to 50) modified di(meth)acrylate, bisphenol S ethylene oxide (repeating number=2 to 50) modified di(meth)acrylate, bisphenol S propylene oxide (repeating number=2 to 50) modified di(meth)acrylate, trimethylolethane tri(meth)acrylate, trimethylolpropane tri(meth)acrylate, trimethylolpropane tricaprolactonate tri(meth)acrylate, trimethylolhexane tri(meth)acrylate, pentaerythritol tri(meth)acrylate, pentaerythritol tetra(meth)acrylate, diglycerine tetra(meth)acrylate, ditrimethylolpropane tetra(meth)acrylate, ditrimethylolpropane tetracaprolactonate, tetra(meth)acrylate, ditrimethylolethane tetra(meth)acrylate, ditrimethylolbutane tetra(meth)acrylate, ditrimethylolhexane tetra (meth)acrylate, dipentaerythritol penta (meth) acrylate, dipentaerythritol hexa(meth)acrylate, tripentaerythritol hexa(meth) acrylate, tripentaerythritol hepta(meth)acrylate, tripentaerythritol octa(meth)acrylate, polyester(meth)acrylates having two or more ethylenically unsaturated double bonds such as divinyl benzene, diisopropenyl benzene, and trivinyl benzene, and urethane oligomers having two or more ethylenically unsaturated double bonds.

The proportion of the component (B) is 20 to 95 mass %, preferably 25 to 70 mass %, more preferably 30 to 50 mass %, with respect to the total amount of the component (A) and the component (B). When the proportion is less than 20 mass %, the polymer of the component (A) and the component (B) is not miscible with an organic solvent such as an oil material. When the proportion exceeds 95 mass %, a flexible film cannot be easily obtained, degrading the usability.

(B-2) Silicone Macromonomer Having Radically Polymerizable Group

The component (B) preferably further includes (B-2) a silicone macromonomer having a radically polymerizable group.

The component (B-2) is preferably a silicone macromonomer shown by the following formula (1),

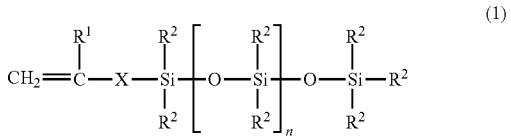

(1)

wherein X represents a divalent aromatic group having 6 to 12 carbon atoms or —COOR$^3$— where R$^3$ represents an aliphatic group bonded to Si; R$_1$ represents a hydrogen atom or a methyl group; R$^2$ may be the same or different and represents a fluorine-substituted or unsubstituted alkyl group having 1 to 30 carbon atoms or an aryl group; and "n" represents an integer of 1 to 300.

In the silicone macromonomer shown by the formula (1), R$^1$ represents a hydrogen atom or a methyl group, preferably a methyl group.

R$^2$ may be the same or different and represents a fluorine-substituted or unsubstituted alkyl group having 1 to 30 carbon atoms or an aryl group; preferably a fluorine-substituted or unsubstituted alkyl group having 1 to 6 carbon atoms or an aryl group in consideration of the skin; more preferably a methyl group, a phenyl group, or a trifluoropropyl group, in consideration of low stimulability and smoothness to the skin; most preferably a methyl group.

X represents —COOR$^3$— or a divalent aromatic group having 6 to 12 carbon atoms, preferably —COOR$^3$— or a divalent aromatic group having 6 to 8 carbon atoms. In —COOR$^3$—, R$^3$ represents an aliphatic group bonded to Si, while the carbonyl group is bonded to a carbon atom of the main chain of the copolymer. Examples of R$^3$ include —(CH$_2$)a-, where "a" represents an integer of 1 to 9, preferably an integer of 2 to 7, more preferably an integer of 3 to 5. Examples of the divalent aromatic group include a phenylene group, a tolylene group, a xylylene group, and a mesitylene group; a phenylene group is preferable. Exemplary macromonomers in which X is —COOR$^3$— or a divalent aromatic group are shown by the following general formulae (2) and (3). In these macromonomers, R$^1$ to R$^3$, "a", and "n" are as defined above.

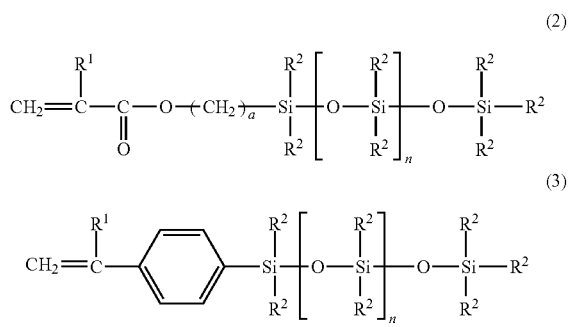

"n" represents an integer of 1 to 300, preferably an integer of 3 to 80, more preferably an integer of 5 to 65. When the upper limit of "n" is 300 or less, reactivity of the polymerization reaction for production is not reduced, and the resulting film-forming composition is not degraded in adhesiveness. Moreover, the above range prevents reduction of miscibility with a hydrocarbon-based oil material when the oil material is blended to the film-forming composition. Thus, this range is preferable. When "n" is 1 or more, sufficient smoothness can be obtained, and the film-forming composition has little stickiness.

The silicone macromonomer shown by the general formula (1), (2), or (3) can be typically obtained by dehydrochlorination reaction of a (meth)acrylate-substituted chlorosilane compound with carbinol-modified silicone according to a usual method, although the synthesis method is not limited thereto.

The proportion of the component (B-2) is preferably 0 to 65 mass %, more preferably 5 to 55 mass %, much more preferably 10 to 50 mass %, with respect to the whole component (B). A proportion of 65 mass % or less prevents reduction of miscibility with an organic oil material, formation of a viscous film, and deterioration of usability.

The component (A) and the component (B) are preferably polymerized in the presence of a radical polymerization initiator such as benzoyl peroxide, lauroyl peroxide, or azobisisobutyronitrile. The polymerization method may be any of solution polymerization process, emulsion polymerization process, suspension polymerization process, and bulk polymerization process. Among them, the solution polymerization process is preferable since the molecular weight of the resulting polymer can be easily adjusted within a desired range. The polymerization reaction may be performed in a solvent. Examples of the solvent used in this reaction include aliphatic organic solvents such as pentane, hexane, decane, dodecane, hexadecane, and octadecane, aromatic organic solvents such as benzene, toluene, and xylene, alcoholic organic solvents such as methanol, ethanol, propanol, butanol, hexanol, and decanol, halogenated organic solvents such as chloroform and carbon tetrachloride, ketone organic solvents such as acetone and methyl ethyl ketone. However, the polymerization is preferably performed without a solvent or with ethanol or isopropanol, in view of use for cosmetics.

The polymer thus produced preferably has a weight average molecular weight of 700 to 500,000, more preferably 2,000 to 300,000, particularly preferably 3,000 to 100,000, by GPC in terms of polystyrene. When the weight average molecular weight is 500,000 or less, miscibility with various oil materials is not reduced. When the weight average molecular weight is 700 or more, feeling of use of the film-forming composition is not degraded. Thus, this range is preferable. The weight average molecular weight can be measured, for example, by liquid gel permeation chromatography (GPC) based on a calibration curve determined from linear polystyrene standards with a refractive index detector using tetrahydrofuran or toluene as an eluent, although the measurement method is not particularly limited thereto.

As described above, the film-forming composition of the present invention, which contains the polymer obtained by polymerizing the component (A) and the component (B), is capable of forming a flexible and transparent film that is excellent in adhesiveness to the skin, hair, or the like and does not exhibit stickiness and secondary adhesion.

Moreover, the film-forming composition of the present invention may further include (C) an oil material. The oil material may be one kind or two or more kinds, and is preferably oil generally used for cosmetics. The oil material may be any of solid, semi-solid, and liquid. Preferably, the oil material is liquid. The film-forming composition of the present invention has little stickiness and excellent water repellency and usability even when the oil material is contained.

Examples of the oil material include silicone oil, hydrocarbon oil, higher fatty acid, polar oil such as ester oil and natural animal and vegetable oil, semi-synthetic oil, and fluorinated oil. More specifically, the oil material is preferably silicone oil, hydrocarbon oil, or a combination thereof, particularly preferably silicone oil, light liquid isoparaffin, or a combination thereof, for these oil materials have good miscibility with the polymer of the component (A) and the component (B).

Examples of the silicone oil include linear or branched organopolysiloxanes having low to high viscosity such as dimethylpolysiloxane, caprylylmethicone, phenyltrimethicone, methylphenylpolysiloxane, methylhexyl-polysiloxane, methylhydrogen polysiloxane, a copolymer of dimethylsiloxane and methylphenylsiloxane, tristrimethylsiloxymethylsilane, and tetrakistrimethylsiloxysilane; cyclic organopolysiloxanes such as octamethylcyclotetrasiloxane, decamethylcyclopentasiloxane, dodecamethylcyclohexa-siloxane, tetramethyltetrahydrogencyclotetrasiloxane, and tetramethyltetraphenylcyclotetrasiloxane; amino-modified organopolysiloxane; silicone rubber such as dimethyl polysiloxane gum with a high degree of polymerization, amino-modified organopolysiloxane gum, and a gummy copolymer of dimethylsiloxane and methylphenylsiloxane; a cyclic polysiloxane solution of silicone gum or rubber, a cyclic organopolysiloxane solution of trimethylsiloxysilicate or trimethylsiloxysilicate, higher alkoxy-modified organopolysiloxane such as stearoxysilicone, higher fatty acid-modified organopolysiloxane, alkyl-modified organopolysiloxane, long chain alkyl-modified organopolysiloxane, fluorine-modified organopolysiloxane, silicone resins, and solutions containing a dissolved silicone resin.

Examples of the hydrocarbon oil include linear or branched volatile hydrocarbon oil. Illustrative examples thereof include ozocerite, α-olefin oligomers, light isoparaffin, isododecane, light liquid isoparaffin, squalane, synthetic squalane, vegetable squalane, squalene, ceresin, paraffin, paraffin wax, polyethylene wax, polyethylene-polypropylene wax, (ethylene/propylene/styrene) copolymers, (butylene/propylene/styrene) copolymers, liquid paraffin, liquid isoparaffin, pristane, polyisobutylene, hydrogenated polyisobutene, microcrystalline wax, and vaseline.

Examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid. Examples of the higher alcohol include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glycerin ether (batyl alcohol), and monooleyl glyceryl ether (selachyl alcohol).

Examples of the ester oil include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroylsarcosinate, and diisostearyl malate. Examples of the glyceride oil include acetoglyceryl, glyceryl triisooctanoate, glyceryl triisostearate, glyceryl triisopalmitate, glyceryl monostearate, glyceryl di-2-heptylundecanoate, glyceryl trimyristate, and diglyceryl myristate isostearate.

Examples of the natural animal and vegetable oil and the semi-synthetic oil include avocado oil, linseed oil, almond oil, insects wax, perilla oil, olive oil, cacao butter, kapok wax, kaya oil, carnauba wax, liver oil, candelilla wax, purified candelilla wax, beef tallow, neat's-foot oil, beef bone fat, cured beef tallow, apricot kernel oil, whale wax, hydrogenated oil, wheat germ oil, sesame oil, rice germ oil, rice bran oil, sugarcane wax, sasanqua oil, safflower oil, shea butter, Chinese tung oil, cinnamon oil, jojoba wax, squalane, squalene, shellac wax, turtle oil, soybean oil, tea seed oil, camellia oil, evening primrose oil, corn oil, pig fat, rapeseed oil, Japanese tung oil, bran wax, germ oil, horse wax, Persic oil, palm oil, palm kernel oil, castor oil, cured castor oil, methyl ester of castor oil fatty acid, sunflower oil, grapeseed oil, bayberry wax, jojoba oil, hydrogenated jojoba oil, macadamia nut oil, bees wax, mink oil, meadowfoam seed oil, cotton seed oil, cotton wax, Japan wax, Japan wax kernel oil, montan wax, coconut oil, cured coconut oil, tri-coconut oil fatty acid glyceride, mutton tallow, peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and egg-yolk oil. POE denotes polyoxyethylene.

Examples of the fluorinated oil material include perfluoro polyether, perfluoro decalin, and perfluoro octane.

The formulation amount of (C) the oil material contained in the film-forming composition of the present invention is preferably 1 to 98 mass %, more preferably 10 to 50 mass %, with respect to the whole film-forming composition.

The oil material (C) may be blended during polymerization of the component (A) and the component (B) unless the polymerization is adversely affected. Alternatively, the oil material may be blended during preparation of the component (A).

<Cosmetic>

Furthermore, the present invention provides a cosmetic containing the above film-forming composition. The formulation amount of the film-forming composition is preferably 0.1 to 30 mass %, more preferably 1 to 25 mass %, particularly preferably 2 to 20 mass %, with respect to the whole cosmetic.

The cosmetic may contain, in addition to the film-forming composition of the present invention, components generally used for cosmetics, for example, component appropriately selected from white pigments, coloring pigments, extender pigments, organic powder, powder raw materials such as pearl agents, tar pigments, surfactants, polymers, gelation agents, thickening agents, UV-absorbing agents, preservatives, polyalcohol, fragrance, and skin benefit agents.

The cosmetic of the present invention, which may be obtained by blending the above cosmetic components, is for example a skin care cosmetic such as a milky lotion, a cream, a cleansing cream, a pack, a massage material, a beauty lotion, a beauty oil, a cleansing lotion, a deodorant, a hand cream, a lip cream, or a wrinkle concealer; a make-up cosmetic such as a make-up foundation, a concealer, a white powder, a liquid foundation, an oily foundation, a cheek rouge, an eye shadow, a mascara, an eye liner, an eye brow, or a lipstick; a hair cosmetic such as a shampoo, a rinse, a treatment, or a setting material; a UV-protective cosmetic such as an antiperspirant, a sunscreen oil, a sunscreen lotion, or a sunscreen cream.

The cosmetic may have various shapes, including liquid, emulsion, cream, solid, paste, gel, powder, pressed material, multilayer, mousse, spray, and stick.

Furthermore, these cosmetics may be present in various forms, including water-based, oil-based, water-in-oil emulsion, oil-in-water emulsion, non-aqueous emulsion, and multi-emulsion such as W/O/W and O/W/O.

EXAMPLE

Hereinafter, the present invention will be more specifically described with reference to synthesis examples, comparative synthesis example, examples, and comparative examples, but the present invention is not limited thereto.

Synthesis Example 1

A reactor was charged with 56 g (0.35 mol) of hexamethyldisiloxane, 22 g (0.09 mol) of 1,3-bis(3-mercaptopropyl)-1,1,3,3-tetramethyldisiloxane, 140 g of ethylpolysilicate containing 40% of $SiO_2$ (corresponding to 0.93 mol of $SiO_2$), and 60 g of isopropyl alcohol, and 1.2 g of methanesulfonic acid was added thereto. The resulting mixture was cooled to 10 to 20° C., and 40 g of water was added dropwise under stirring. After dropwise addition, the mixture was heated at 70 to 90° C. for 6 hours to perform hydrolysis. After neutralizing the acid with potassium hydroxide and calcium carbonate, 100 g of decamethylcyclopentasiloxane was added, and the resulting mixture was heated to 120° C. to remove produced ethanol, isopropyl alcohol, and excess water. The resultant was cooled and then diluted with decamethylcyclopentasiloxane. The dilution was filtered to obtain 300 g of a decamethylcyclopentasiloxane solution containing 70% of a silicone resin. 200 g of this solution was heated at 120° C. under reduced pressure to remove decamethylcyclopentasiloxane. 130 g of a powder silicone resin was thus obtained. The weight average molecular weight of this resin was 4,900, as measured by GPC in terms of polystyrene standards.

Synthesis Example 2

A reactor was charged with 61 g (0.38 mol) of hexamethyldisiloxane, 2.2 g (0.0092 mol) of 1,3-bis(3-mercaptopropyl)-1,1,3,3-tetramethyldisiloxane, 140 g of ethylpolysilicate containing 40% of $SiO_2$ (corresponding to 0.93 mol of $SiO_2$), and 60 g of isopropyl alcohol, and 1.2 g of methanesulfonic acid was added thereto. The resulting mixture was cooled to 10 to 20° C., and 40 g of water was added dropwise under stirring. After dropwise addition, the mixture was heated at 70 to 90° C. for 6 hours to perform hydrolysis. After neutralizing the acid with potassium hydroxide and calcium carbonate, 100 g of decamethylcyclopentasiloxane was added, and the resulting mixture was heated to 120° C. to remove produced ethanol, isopropyl alcohol, and excess water. The resultant was cooled and then diluted with decamethylcyclopentasiloxane. The dilution was filtered to obtain 310 g of a decamethylcyclopentasiloxane solution containing 68% of a silicone resin. 200 g of this solution was heated at 120° C. under reduced pressure to remove decamethylcyclopentasiloxane. 130 g of a powder silicone resin was thus obtained. The weight average molecular weight of this resin was 3,800, as measured by GPC in terms of polystyrene standards.

Comparative Synthesis Example 1

A reactor was charged with 62 g (0.38 mol) of hexamethyldisiloxane, 140 g of ethylpolysilicate containing 40% of $SiO_2$ (corresponding to 0.93 mol of $SiO_2$), and 60 g of isopropyl alcohol, and 1.2 g of methanesulfonic acid was added thereto. The resulting mixture was cooled to 10 to 20° C., and 120 g of water was added dropwise under stirring. After dropwise addition, the mixture was heated at 70 to 90° C. for 6 hours to perform hydrolysis. After neutralizing the acid with potassium hydroxide and calcium carbonate, 100 g of decamethylcyclopentasiloxane was added, and the resulting mixture was heated to 120° C. to remove produced ethanol, isopropyl alcohol, and excess water. The resultant was cooled and then diluted with decamethylcyclopentasiloxane. The dilution was filtered to obtain 300 g of a decamethylcyclopentasiloxane solution containing 70% of a silicone resin. 200 g of this solution was heated at 120° C. under reduced pressure to remove decamethylcyclopentasiloxane. 136 g of a powder silicone resin was thus obtained. The weight average molecular weight of this resin was 4,500, as measured by GPC in terms of polystyrene standards.

Examples 1 to 5 and Comparative Examples 1 to 3

A glass flask equipped with a stirrer, a thermometer, and a reflux condenser was charged with 140 g of isopropanol, monomers shown in Table 1, and 4 g of t-butylperoxy-2-ethylhexanoate and heated at 82° C. to reflux the mixture while stirring in nitrogen gas stream. After 5 hours of reaction, volatile components were distilled off under reduced pressure to obtain an acrylic silicone copolymer. The weight average molecular weight was measured by GPC (in terms of polystyrene standards).

TABLE 1

| | Component | | Example 1 | Example 2 | Example 3 | Example 4 | Example 5 | Comparative example 1 | Comparative example 2 | Comparative example 3 |
|---|---|---|---|---|---|---|---|---|---|---|
| Silicone resin | (A) | Synthesis example 1 | 9 | 9 | | | | | | |
| | | Synthesis example 2 | | | 9 | 50 | 80 | 90 | | |
| | | Comparative synthesis example 1 | | | | | | | | 9 |
| Radically polymerizable monomer | (B-1) | methyl methacrylate | 27 | 18 | 27 | 15 | 5 | 3 | 27 | 30 |
| | | isobutyl methacrylate | 14 | 9 | 14 | 7 | 5 | 2 | 14 | 15 |
| | | 2-hydroxyethyl methacrylate | | 9 | | | | | | |
| | | 2-ethylhexyl methacrylate | 5 | | 5 | 3 | 10 | 1 | 5 | 5 |
| | | n-stearyl methacrylate | | 9 | | | | | | |
| | (B-2) | Silicone macro-monomer 1 | 45 | | 45 | 25 | | 4 | 45 | 50 |
| | | Silicone macro-monomer 2 | | 46 | | | | | | |
| | Weight average molecular weight | | 115,000 | 90,000 | 65,000 | 11,000 | 9,000 | 8,000 | 50,000 | 48,000 |

In Table 1, the value of each component is expressed by mass % with respect to the total amount of the component (A) and the component (B).

(Silicone macromonomer 1)

$$CH_2=\overset{CH_3}{\underset{\underset{O}{\|}}{C}}-C-O-C_3H_6-\underset{CH_3}{\overset{CH_3}{Si}}-\left[O-\underset{CH_3}{\overset{CH_3}{Si}}\right]_n-O-\underset{CH_3}{\overset{CH_3}{Si}}-CH_3$$

n ≈ 30

(Silicone macromonomer 2)

$$CH_2=\overset{CH_3}{\underset{}{C}}-\phantom{X}\!\!\!\!\!\!\!\!\!\!\!\!\!\!\!\text{(C}_6\text{H}_4\text{)}-\underset{CH_3}{\overset{CH_3}{Si}}-\left[O-\underset{CH_3}{\overset{CH_3}{Si}}\right]_n-O-\underset{CH_3}{\overset{CH_3}{Si}}-CH_3$$

n ≈ 30

Comparative Example 3-1

12.5 mass parts of the silicone resin in synthesis example 1 and 87.5 mass parts of the copolymer in comparative example 3 were mixed to obtain a mixture of comparative example 3-1.

Comparative Example 3-2

12.5 mass parts of the silicone resin in synthesis example 2 and 87.5 mass parts of the copolymer in comparative example 3 were mixed to obtain a mixture of comparative example 3-2.

Evaluation by Heating and Drying Film Formation Method

The polymers (examples 1 to 5, comparative examples 1 and 2) and the mixtures (comparative examples 3-1 and 3-2) were each dissolved in decamethylcyclopentasiloxane to prepare film-forming compositions with a concentration of 30%. 6 g of the film-forming composition was put on an aluminum plate with a diameter of 60 mm and dried at 105° C. for 3 hours. Then, the state of the formed film was observed to evaluate the flexibility. The result is given in Table 2.

TABLE 2

| | Resin | | | | | | | | |
|---|---|---|---|---|---|---|---|---|---|
| | Example 1 | Example 2 | Example 3 | Example 4 | Example 5 | Comparative example 1 | Comparative example 2 | Comparative example 3-1 | Comparative example 3-2 |
| Transparency | transparent | transparent | transparent | transparent | transparent | white powder | white film | white film | white film |
| Flexibility | good | good | good | good | good | poor | fair | fair | fair | good: no cracks occurred on bending, fair: cracks occurred on several bending, poor: cracks occurred on one bending As shown in Table 2, comparative example 1, where the component (A) was contained in an amount of 90 mass % with respect to the total amount of the component (A) and the component (B), resulted in white powder without flexibility. Moreover, comparative example 2, where the silicone resin contained no —C$_3$H$_6$SH group, and comparative examples 3-1 and 3-2, where the component (A) was mixed with the polymer of only the component (B), could form a film but had poor transparency and flexibility. In contrast, examples 1 to 5 could form a transparent film having high flexibility.

Evaluation by Skin Application Film Forming Method

The polymers (examples 1 to 5, comparative examples 1 and 2) and the mixtures (comparative examples 3-1 and 3-2) were each dissolved in decamethylcyclopentasiloxane to prepare film-forming compositions with a concentration of 10%. 0.1 g of the film-forming composition was uniformly applied to the skin and allowed to stand for 1 hour. Then, transparency, stickiness, and abrasion resistance of the formed film were evaluated by the following criteria. The result is given in Table 3.

Film Criteria (1) Transparency: Transparency of the film was visually evaluated.
A: Transparent
B: Hardly cloudy
C: Slightly cloudy
D: Cloudy
(2) Stickiness: Stickiness and smoothness were evaluated by touching the surface of the film with a finger pad.
A: Not-sticky and favorably slick
B: Hardly sticky and slightly slick
C: Slightly sticky and hardly slick
D: Sticky and not-slick
(3) Abrasion Resistance: The surface of the film was lightly scrubbed by a finger nail to check whether the film was damaged.
A: Not damaged
B: Hardly damaged
C: Slightly damaged
D: Damaged

TABLE 3

|  | Example 1 | Example 2 | Example 3 | Example 4 | Example 5 | Comparative example 1 | Comparative example 2 | Comparative example 3-1 | Comparative example 3-2 |
| --- | --- | --- | --- | --- | --- | --- | --- | --- | --- |
| Transparency | A | A | A | A | A | D | D | C | D |
| Stickiness | A | B | A | B | B | C | B | D | D |
| Abrasion resistance | A | A | A | A | B | A | C | C | D |

As shown in Table 3, comparative examples 1, 2, 3-1, and 3-2 failed to obtain a film satisfying all the criterion of appearance, stickiness, and abrasion resistance. In contrast, examples 1 to 5 could form a transparent film with non-stickiness and high abrasion resistance.

The above results demonstrated that the film-forming composition of the present invention shown in examples 1 to 5 could form a highly transparent film having high flexibility and non-stickiness. That is, the film-forming composition of the present invention is capable of forming a transparent film that is excellent in adhesiveness to the skin, hair, or the like and does not exhibit stickiness and secondary adhesion.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A film-forming composition comprising a polymer obtained by polymerizing:

(A) 5 to 80 mass % of a silicone resin having an $R_3SiO_{1/2}$ unit, an $R_2R'SiO_{1/2}$ unit, and an $SiO_2$ unit, where R may be the same or different and represents a monovalent hydrocarbon group having 1 to 6 carbon atoms, and R' represents a —$C_3H_6SH$ group, in which a total amount of the $R_3SiO_{1/2}$ unit, the $R_2R'SiO_{1/2}$ unit, and the $SiO_2$ unit is 80 mol % or more with respect to all structural units, and a mole ratio expressed by (sum of $R_3SiO_{1/2}$ unit and $R_2R'SiO_{1/2}$ unit)/($SiO_2$ unit) ranges from 0.5 to 1.5; and (B) 20 to 95 mass % of one or more radically polymerizable compounds, wherein
the component (B) includes (B-1) one or more radically polymerizable monomers having no SiO unit in a structure thereof.

2. The film-forming composition according to claim 1, wherein the component (B-1) includes methyl (meth)acrylate.

3. The film-forming composition according to claim 2, wherein the component (B) further includes (B-2) a silicone macromonomer having a radically polymerizable group.

4. The film-forming composition according to claim 3, wherein the component (B-2) is a silicone macromonomer shown by the following formula (1),

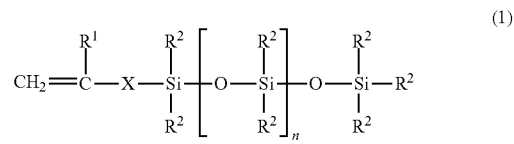

wherein X represents a divalent aromatic group having 6 to 12 carbon atoms or —$COOR^3$— where $R^3$ represents an aliphatic group bonded to Si; $R^1$ represents a hydrogen atom or a methyl group; $R^2$ may be the same or different and represents a fluorine-substituted or unsubstituted alkyl group having 1 to 30 carbon atoms or an aryl group; and "n" represents an integer of 1 to 300.

5. The film-forming composition according to claim 4, further comprising (C) an oil material in an amount of 1 to 98 mass % with respect to the whole film-forming composition.

6. The film-forming composition according to claim 5, wherein the component (C) is silicone oil, light liquid isoparaffin, or both of the silicone oil and the light liquid isoparaffin.

7. The film-forming composition according to claim 3, further comprising (C) an oil material in an amount of 1 to 98 mass % with respect to the whole film-forming composition.

8. The film-forming composition according to claim 7, wherein the component (C) is silicone oil, light liquid isoparaffin, or both of the silicone oil and the light liquid isoparaffin.

9. The film-forming composition according to claim 2, further comprising (C) an oil material in an amount of 1 to 98 mass % with respect to the whole film-forming composition.

10. The film-forming composition according to claim 9, wherein the component (C) is silicone oil, light liquid isoparaffin, or both of the silicone oil and the light liquid isoparaffin.

11. A cosmetic comprising the film-forming composition according to claim 2.

12. The film-forming composition according to claim 1, wherein the component (B) further includes (B-2) a silicone macromonomer having a radically polymerizable group.

13. The film-forming composition according to claim 12, wherein the component (B-2) is a silicone macromonomer shown by the following formula (1),

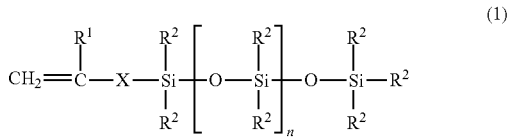
(1)

wherein X represents a divalent aromatic group having 6 to 12 carbon atoms or —COOR³— where R³ represents an aliphatic group bonded to Si; R¹ represents a hydrogen atom or a methyl group; R² may be the same or different and represents a fluorine-substituted or unsubstituted alkyl group having 1 to 30 carbon atoms or an aryl group; and "n" represents an integer of 1 to 300.

14. The film-forming composition according to claim 13, further comprising (C) an oil material in an amount of 1 to 98 mass % with respect to the whole film-forming composition.

15. The film-forming composition according to claim 14, wherein the component (C) is silicone oil, light liquid isoparaffin, or both of the silicone oil and the light liquid isoparaffin.

16. The film-forming composition according to claim 12, further comprising (C) an oil material in an amount of 1 to 98 mass % with respect to the whole film-forming composition.

17. The film-forming composition according to claim 16, wherein the component (C) is silicone oil, light liquid isoparaffin, or both of the silicone oil and the light liquid isoparaffin.

18. The film-forming composition according to claim 1, further comprising (C) an oil material in an amount of 1 to 98 mass % with respect to the whole film-forming composition.

19. The film-forming composition according to claim 18, wherein the component (C) is silicone oil, light liquid isoparaffin, or both of the silicone oil and the light liquid isoparaffin.

20. A cosmetic comprising the film-forming composition according to claim 1.

* * * * *